United States Patent
Hovda et al.

(10) Patent No.: US 11,364,129 B2
(45) Date of Patent: Jun. 21, 2022

(54) METHOD AND SPACER DEVICE FOR SPANNING A SPACE FORMED UPON REMOVAL OF AN INTERVERTEBRAL DISC

(71) Applicant: Simplify Medical Pty Ltd, Paddington (AU)

(72) Inventors: David Hovda, Mountain View, CA (US); Yves Arramon, Sunnyvale, CA (US)

(73) Assignee: Simplify Medical Pty Ltd, Melbourne (AU)

( * ) Notice: Subject to any disclaimer, the term of this patent is extended or adjusted under 35 U.S.C. 154(b) by 0 days.

(21) Appl. No.: 15/359,298

(22) Filed: Nov. 22, 2016

(65) Prior Publication Data

US 2017/0071757 A1    Mar. 16, 2017

Related U.S. Application Data

(63) Continuation of application No. 12/255,731, filed on Oct. 22, 2008, now abandoned.

(Continued)

(51) Int. Cl.
| | | |
|---|---|---|
| *A61F 2/44* | (2006.01) | |
| *A61F 2/30* | (2006.01) | |
| *A61B 17/86* | (2006.01) | |

(52) U.S. Cl.
CPC ........ *A61F 2/4465* (2013.01); *A61F 2/30771* (2013.01); *A61B 17/86* (2013.01);
(Continued)

(58) Field of Classification Search
CPC ......... A61F 2/44–447; A61F 2002/4475–4495
See application file for complete search history.

(56) References Cited

U.S. PATENT DOCUMENTS 3,867,728 A * 2/1975 Stubstad ............. A61F 2/30907
                                                     128/DIG. 21
4,309,777 A    1/1982 Patil
(Continued)

FOREIGN PATENT DOCUMENTS

| DE | 3023353 A1 | 4/1981 |
| DE | 10035182 A1 | 2/2002 |

(Continued)

OTHER PUBLICATIONS

Buttner-Janz, The Development of the Artificial Disc. Introduction, pp. 1-18, Library of Congress Catalogue No. 92-75582, ISBN 0-9635430-0-8 (1989).

(Continued)

*Primary Examiner* — Eduardo C Robert
*Assistant Examiner* — Steven J Cotroneo
(74) *Attorney, Agent, or Firm* — Hoffman Warnick LLC

(57) ABSTRACT

An intervertebral spacer is designed particularly for patients who are not candidates for total disc replacement. The spacer maintains disc height and prevents subsidence with a large vertebral body contacting surface area while substantially reducing recovery time by eliminating the need for bridging bone. The intervertebral spacer or fusion spacer includes a rigid spacer body sized and shaped to fit within an intervertebral space between two vertebral bodies. In one embodiment, the spacer body has two opposed metallic vertebral contacting surfaces, at least one fin extending from each of the vertebral contacting surfaces and configured to be positioned within slots cut into the two vertebral bodies. Holes, if present, cover less than 40 percent of the entire vertebral body contacting surfaces to provide increased bone ongrowth surfaces and to prevent subsidence.

21 Claims, 6 Drawing Sheets

Related U.S. Application Data

(60) Provisional application No. 60/981,665, filed on Oct. 22, 2007.

(52) U.S. Cl.
CPC ............ *A61F 2002/30056* (2013.01); *A61F 2002/30772* (2013.01); *A61F 2002/30787* (2013.01); *A61F 2002/30884* (2013.01); *A61F 2002/30899* (2013.01); *A61F 2002/30904* (2013.01); *A61F 2002/449* (2013.01); *A61F 2250/0032* (2013.01); *A61F 2310/00017* (2013.01); *A61F 2310/00023* (2013.01); *A61F 2310/00029* (2013.01); *A61F 2310/00071* (2013.01); *A61F 2310/0088* (2013.01); *A61F 2310/00131* (2013.01); *A61F 2310/00179* (2013.01); *A61F 2310/00407* (2013.01); *A61F 2310/00431* (2013.01); *A61F 2310/00604* (2013.01); *A61F 2310/00796* (2013.01); *A61F 2310/00976* (2013.01)

(56) References Cited

U.S. PATENT DOCUMENTS

| | | | |
|---|---|---|---|
| 4,531,917 | A | 7/1985 | Linkow et al. |
| 4,566,466 | A | 1/1986 | Ripple et al. |
| 4,619,660 | A | 10/1986 | Christiansen et al. |
| 4,673,407 | A | 6/1987 | Martin |
| 4,759,766 | A | 7/1988 | Buettner-Janz et al. |
| 4,759,769 | A | 7/1988 | Hedman et al. |
| 4,834,757 | A | 5/1989 | Brantigan |
| 4,863,477 | A | 9/1989 | Monson |
| 4,904,261 | A | 2/1990 | Dove et al. |
| 4,917,704 | A * | 4/1990 | Frey .................. A61F 2/442 |
| | | | 606/247 |
| 4,932,969 | A | 6/1990 | Frey et al. |
| 4,946,378 | A | 8/1990 | Hirayama et al. |
| 4,997,432 | A | 3/1991 | Keller |
| 5,035,716 | A | 7/1991 | Downey |
| 5,057,108 | A | 10/1991 | Shetty et al. |
| 5,071,437 | A | 12/1991 | Steffee |
| 5,122,130 | A | 6/1992 | Keller |
| 5,192,327 | A | 3/1993 | Brantigan |
| 5,195,526 | A | 3/1993 | Michelson |
| 5,258,031 | A | 11/1993 | Salib et al. |
| 5,282,861 | A | 2/1994 | Kaplan |
| 5,306,308 | A | 4/1994 | Gross et al. |
| 5,314,477 | A * | 5/1994 | Marnay ............... A61F 2/4425 |
| | | | 623/17.15 |
| 5,320,644 | A | 6/1994 | Baumgartner |
| 5,370,697 | A * | 12/1994 | Baumgartner ........ A61F 2/442 |
| | | | 623/17.15 |
| 5,394,457 | A | 2/1995 | Leibinger et al. |
| 5,401,269 | A | 3/1995 | Buettner-Janz et al. |
| 5,415,704 | A | 5/1995 | Davidson |
| 5,423,816 | A | 6/1995 | Lin |
| 5,458,642 | A | 10/1995 | Beer et al. |
| 5,462,575 | A | 10/1995 | Del Corso |
| 5,484,437 | A | 1/1996 | Michelson |
| 5,489,307 | A | 2/1996 | Kuslich et al. |
| 5,505,732 | A | 4/1996 | Michelson |
| 5,507,816 | A | 4/1996 | Bullivant |
| 5,534,030 | A | 7/1996 | Navarro et al. |
| 5,556,431 | A | 9/1996 | Büttner-Janz |
| 5,674,296 | A | 10/1997 | Bryan et al. |
| 5,676,701 | A | 10/1997 | Yuan et al. |
| 5,676,702 | A | 10/1997 | Ratron |
| 5,683,465 | A | 11/1997 | Shinn et al. |
| 5,702,450 | A | 12/1997 | Bisserie |
| 5,709,683 | A | 1/1998 | Bagby |
| 5,728,159 | A | 3/1998 | Stroever et al. |
| 5,741,253 | A | 4/1998 | Michelson |
| 5,776,198 | A | 7/1998 | Rabbe et al. |
| 5,782,832 | A | 7/1998 | Larsen et al. |
| 5,797,909 | A | 8/1998 | Michelson |
| 5,797,917 | A | 8/1998 | Boyd et al. |
| 5,824,094 | A * | 10/1998 | Serhan .................. A61F 2/442 |
| | | | 623/17.16 |
| 5,836,948 | A | 11/1998 | Zucherman et al. |
| 5,865,846 | A | 2/1999 | Bryan et al. |
| 5,865,848 | A | 2/1999 | Baker |
| 5,888,226 | A | 3/1999 | Rogozinski |
| 5,895,428 | A | 4/1999 | Berry |
| 5,899,901 | A | 5/1999 | Middleton |
| 5,899,911 | A | 5/1999 | Carter |
| 5,928,284 | A | 7/1999 | Mehdizadeh |
| 5,989,251 | A | 11/1999 | Nichols |
| 5,989,291 | A | 11/1999 | Ralph et al. |
| 6,001,130 | A | 12/1999 | Bryan et al. |
| 6,019,792 | A | 2/2000 | Cauthen |
| 6,022,376 | A | 2/2000 | Assell et al. |
| 6,039,761 | A | 3/2000 | Li et al. |
| 6,039,763 | A | 3/2000 | Shelokov |
| 6,080,155 | A | 6/2000 | Michelson |
| 6,083,228 | A | 7/2000 | Michelson |
| 6,086,613 | A | 7/2000 | Camino et al. |
| 6,096,038 | A | 8/2000 | Michelson |
| 6,106,557 | A | 8/2000 | Robioneck et al. |
| 6,132,465 | A | 10/2000 | Ray et al. |
| 6,136,031 | A | 10/2000 | Middleton |
| 6,139,551 | A | 10/2000 | Michelson et al. |
| 6,139,579 | A | 10/2000 | Steffee et al. |
| 6,143,033 | A | 11/2000 | Paul et al. |
| 6,146,421 | A | 11/2000 | Gordon et al. |
| 6,156,067 | A | 12/2000 | Bryan et al. |
| 6,159,211 | A | 12/2000 | Boriani et al. |
| 6,159,214 | A | 12/2000 | Michelson |
| 6,162,252 | A | 12/2000 | Kuras et al. |
| 6,174,311 | B1 | 1/2001 | Branch et al. |
| 6,176,881 | B1 | 1/2001 | Schaer et al. |
| 6,193,757 | B1 | 2/2001 | Foley et al. |
| 6,224,595 | B1 | 5/2001 | Michelson |
| 6,224,607 | B1 | 5/2001 | Michelson |
| 6,231,609 | B1 | 5/2001 | Mehdizadeh |
| 6,235,030 | B1 | 5/2001 | Zucherman et al. |
| 6,261,296 | B1 | 7/2001 | Aebi et al. |
| 6,264,695 | B1 | 7/2001 | Stoy |
| 6,290,726 | B1 | 9/2001 | Pope et al. |
| 6,296,664 | B1 | 10/2001 | Middleton |
| 6,315,797 | B1 | 11/2001 | Middleton |
| 6,322,567 | B1 | 11/2001 | Mittelstadt et al. |
| 6,336,941 | B1 | 1/2002 | Subba et al. |
| 6,348,071 | B1 | 2/2002 | Steffee et al. |
| 6,368,350 | B1 | 4/2002 | Erickson et al. |
| 6,368,351 | B1 | 4/2002 | Glenn et al. |
| 6,375,681 | B1 | 4/2002 | Truscott |
| 6,375,682 | B1 | 4/2002 | Fleischmann et al. |
| 6,395,032 | B1 | 5/2002 | Gauchet |
| 6,402,785 | B1 | 6/2002 | Zdeblick et al. |
| 6,409,766 | B1 | 6/2002 | Brett |
| 6,413,278 | B1 | 7/2002 | Marchosky |
| 6,416,551 | B1 | 7/2002 | Keller |
| 6,436,098 | B1 | 8/2002 | Michelson |
| 6,440,139 | B2 | 8/2002 | Michelson |
| 6,447,544 | B1 | 9/2002 | Michelson |
| 6,478,800 | B1 | 11/2002 | Fraser et al. |
| 6,517,544 | B1 | 2/2003 | Michelson |
| 6,517,580 | B1 | 2/2003 | Ramadan et al. |
| 6,520,967 | B1 | 2/2003 | Cauthen |
| 6,520,996 | B1 | 2/2003 | Manasas et al. |
| 6,527,804 | B1 | 3/2003 | Gauchet et al. |
| 6,533,817 | B1 | 3/2003 | Norton et al. |
| 6,537,279 | B1 | 3/2003 | Michelson |
| 6,554,863 | B2 | 4/2003 | Paul et al. |
| 6,562,047 | B2 | 5/2003 | Ralph et al. |
| 6,562,074 | B2 | 5/2003 | Gerbec et al. |
| 6,565,574 | B2 | 5/2003 | Michelson |
| 6,579,321 | B1 | 6/2003 | Gordon et al. |
| 6,582,466 | B1 | 6/2003 | Gauchet |
| 6,582,468 | B1 * | 6/2003 | Gauchet ............ A61F 2/30742 |
| | | | 606/309 |
| 6,592,624 | B1 * | 7/2003 | Fraser .................. A61F 2/442 |
| | | | 623/17.16 |

(56) References Cited

U.S. PATENT DOCUMENTS

| | | | |
|---|---|---|---|
| 6,599,294 B2 | 7/2003 | Fuss et al. | |
| 6,607,558 B2 | 8/2003 | Kuras | |
| 6,607,559 B2 | 8/2003 | Ralph et al. | |
| 6,610,092 B2 | 8/2003 | Ralph et al. | |
| 6,623,525 B2 | 9/2003 | Ralph et al. | |
| 6,645,248 B2 | 11/2003 | Casutt | |
| 6,648,895 B2 | 11/2003 | Burkus et al. | |
| 6,652,533 B2 | 11/2003 | O'Neil | |
| 6,660,038 B2 | 12/2003 | Boyer et al. | |
| 6,666,866 B2 | 12/2003 | Martz et al. | |
| 6,669,731 B2 | 12/2003 | Ralph et al. | |
| 6,669,732 B2 | 12/2003 | Serhan et al. | |
| 6,673,113 B2 | 1/2004 | Ralph et al. | |
| 6,682,562 B2 | 1/2004 | Viart et al. | |
| 6,689,132 B2 | 2/2004 | Biscup | |
| 6,706,068 B2 | 3/2004 | Ferree | |
| 6,709,439 B2 | 3/2004 | Rogers et al. | |
| 6,712,819 B2 | 3/2004 | Zucherman et al. | |
| 6,712,825 B2 | 3/2004 | Aebi et al. | |
| 6,719,794 B2 | 4/2004 | Gerber et al. | |
| 6,723,097 B2 | 4/2004 | Fraser et al. | |
| 6,726,720 B2 | 4/2004 | Ross et al. | |
| 6,726,721 B2 | 4/2004 | Stoy et al. | |
| 6,733,532 B1 | 5/2004 | Gauchet et al. | |
| 6,740,118 B2 * | 5/2004 | Eisermann | A61F 2/4425 623/17.14 |
| 6,740,119 B2 | 5/2004 | Ralph et al. | |
| 6,752,832 B2 | 6/2004 | Neumann | |
| 6,755,841 B2 | 6/2004 | Fraser et al. | |
| 6,764,512 B2 | 7/2004 | Keller | |
| 6,764,515 B2 | 7/2004 | Ralph et al. | |
| 6,770,095 B2 | 8/2004 | Grinberg et al. | |
| 6,790,233 B2 | 9/2004 | Brodke et al. | |
| 6,793,678 B2 | 9/2004 | Hawkins | |
| 6,814,737 B2 | 11/2004 | Cauthen | |
| 6,821,298 B1 | 11/2004 | Jackson | |
| 6,827,740 B1 | 12/2004 | Michelson | |
| 6,830,570 B1 | 12/2004 | Frey et al. | |
| 6,835,206 B2 | 12/2004 | Jackson | |
| 6,846,328 B2 | 1/2005 | Cauthen | |
| 6,852,126 B2 | 2/2005 | Ahlgren | |
| 6,863,673 B2 | 3/2005 | Gerbec et al. | |
| 6,875,213 B2 | 4/2005 | Michelson | |
| 6,896,680 B2 | 5/2005 | Michelson | |
| 6,899,735 B2 | 5/2005 | Coates et al. | |
| 6,936,071 B1 | 8/2005 | Marnay et al. | |
| 6,936,132 B2 | 8/2005 | Topolnitsky | |
| 6,964,686 B2 | 11/2005 | Gordon | |
| 6,966,929 B2 | 11/2005 | Mitchell | |
| 6,966,931 B2 | 11/2005 | Huang | |
| 6,986,788 B2 | 1/2006 | Paul et al. | |
| 6,989,011 B2 | 1/2006 | Paul et al. | |
| 6,994,727 B2 | 2/2006 | Khandkar et al. | |
| 7,011,684 B2 | 3/2006 | Eckman | |
| 7,022,138 B2 | 4/2006 | Mashburn | |
| 7,025,787 B2 | 4/2006 | Bryan et al. | |
| 7,044,972 B2 * | 5/2006 | Mathys, Jr. | A61F 2/4455 623/17.11 |
| 7,044,983 B1 | 5/2006 | Cheng | |
| 7,056,344 B2 | 6/2006 | Huppert et al. | |
| 7,060,073 B2 | 6/2006 | Frey et al. | |
| 7,066,958 B2 | 6/2006 | Ferree | |
| 7,081,120 B2 | 7/2006 | Li et al. | |
| 7,083,651 B2 | 8/2006 | Diaz et al. | |
| 7,087,055 B2 | 8/2006 | Lim et al. | |
| 7,097,648 B1 | 8/2006 | Globerman et al. | |
| 7,115,132 B2 | 10/2006 | Errico et al. | |
| 7,118,580 B1 | 10/2006 | Beyersdorff et al. | |
| 7,147,665 B1 | 12/2006 | Bryan et al. | |
| 7,153,325 B2 | 12/2006 | Kim et al. | |
| 7,169,182 B2 | 1/2007 | Errico et al. | |
| 7,179,294 B2 | 2/2007 | Eisermann et al. | |
| 7,182,784 B2 | 2/2007 | Evans et al. | |
| 7,198,644 B2 | 4/2007 | Schultz et al. | |
| 7,207,991 B2 | 4/2007 | Michelson | |
| 7,214,244 B2 | 5/2007 | Zubok et al. | |
| 7,217,291 B2 | 5/2007 | Zucherman et al. | |
| 7,235,082 B2 | 6/2007 | Bartish et al. | |
| 7,235,101 B2 | 6/2007 | Berry et al. | |
| 7,235,103 B2 | 6/2007 | Rivin | |
| 7,250,060 B2 * | 7/2007 | Trieu | A61F 2/442 623/17.11 |
| 7,255,714 B2 | 8/2007 | Malek | |
| 7,261,739 B2 | 8/2007 | Ralph et al. | |
| 7,267,688 B2 | 9/2007 | Ferree | |
| 7,270,679 B2 | 9/2007 | Istephanous et al. | |
| 7,270,682 B2 | 9/2007 | Frigg et al. | |
| 7,303,582 B2 | 12/2007 | Brady et al. | |
| 7,303,583 B1 | 12/2007 | Schaer et al. | |
| 7,309,358 B2 | 12/2007 | Berry et al. | |
| 7,318,839 B2 | 1/2008 | Malberg et al. | |
| 7,326,250 B2 | 2/2008 | Beaurain et al. | |
| 7,331,994 B2 | 2/2008 | Gordon et al. | |
| 7,331,995 B2 | 2/2008 | Eisermann et al. | |
| 7,429,270 B2 | 9/2008 | Baumgartner et al. | |
| 7,442,211 B2 | 10/2008 | De et al. | |
| 7,452,380 B2 | 11/2008 | Zubok et al. | |
| 7,491,241 B2 | 2/2009 | Errico et al. | |
| 7,494,508 B2 | 2/2009 | Zeegers et al. | |
| 7,517,363 B2 | 4/2009 | Rogers et al. | |
| 7,531,001 B2 | 5/2009 | De et al. | |
| 7,549,995 B2 | 6/2009 | Schultz | |
| 7,563,284 B2 | 7/2009 | Coppes et al. | |
| 7,563,286 B2 | 7/2009 | Gerber et al. | |
| 7,575,598 B2 | 8/2009 | Rothman et al. | |
| 7,578,848 B2 | 8/2009 | Rothman et al. | |
| 7,585,324 B2 | 9/2009 | Rothman et al. | |
| 7,585,326 B2 | 9/2009 | De et al. | |
| 7,615,078 B2 | 11/2009 | White et al. | |
| 7,635,368 B2 * | 12/2009 | Errico | A61F 2/4611 606/86 A |
| 7,637,913 B2 | 12/2009 | De et al. | |
| 7,655,045 B2 * | 2/2010 | Richelsoph | A61F 2/4425 623/17.13 |
| 7,708,776 B1 | 5/2010 | Blain et al. | |
| 7,708,777 B2 | 5/2010 | O'Neil et al. | |
| 7,731,753 B2 | 6/2010 | Reo et al. | |
| 7,731,754 B2 | 6/2010 | De et al. | |
| 7,749,272 B2 * | 7/2010 | Robie | A61L 27/08 623/17.11 |
| 7,763,055 B2 * | 7/2010 | Foley | A61B 17/00234 606/279 |
| 7,819,922 B2 | 10/2010 | Sweeney | |
| 8,057,545 B2 * | 11/2011 | Hughes | A61F 2/4455 623/17.11 |
| 8,092,534 B2 * | 1/2012 | Eckhardt | A61F 2/4425 623/17.11 |
| 8,142,505 B2 | 3/2012 | Tauber | |
| 8,298,287 B2 | 10/2012 | Moumene et al. | |
| 8,491,637 B2 | 7/2013 | Matthis et al. | |
| 8,758,441 B2 | 6/2014 | Hovda et al. | |
| 8,771,357 B2 | 7/2014 | Biedermann et al. | |
| 8,998,990 B2 * | 4/2015 | Bertagnoli | A61B 17/1671 623/17.16 |
| 2001/0016773 A1 | 8/2001 | Serhan et al. | |
| 2001/0029377 A1 | 10/2001 | Aebi et al. | |
| 2001/0051829 A1 | 12/2001 | Middleton | |
| 2002/0022845 A1 | 2/2002 | Zdeblick et al. | |
| 2002/0035400 A1 | 3/2002 | Bryan et al. | |
| 2002/0045904 A1 | 4/2002 | Fuss et al. | |
| 2002/0068936 A1 | 6/2002 | Burkus et al. | |
| 2002/0091392 A1 | 7/2002 | Michelson | |
| 2002/0116009 A1 | 8/2002 | Fraser et al. | |
| 2002/0123753 A1 | 9/2002 | Michelson | |
| 2002/0128715 A1 | 9/2002 | Bryan et al. | |
| 2002/0165550 A1 | 11/2002 | Frey et al. | |
| 2002/0177897 A1 | 11/2002 | Michelson | |
| 2002/0198532 A1 | 12/2002 | Michelson | |
| 2003/0009224 A1 | 1/2003 | Kuras | |
| 2003/0014116 A1 * | 1/2003 | Ralph | A61F 2/4611 623/17.16 |
| 2003/0023245 A1 | 1/2003 | Ralph et al. | |
| 2003/0028249 A1 | 2/2003 | Baccelli et al. | |

(56) References Cited

U.S. PATENT DOCUMENTS

| | | |
|---|---|---|
| 2003/0040746 A1 | 2/2003 | Mitchell et al. |
| 2003/0045884 A1 | 3/2003 | Robie et al. |
| 2003/0045939 A1 | 3/2003 | Casutt |
| 2003/0074076 A1 | 4/2003 | Ferree et al. |
| 2003/0083747 A1 | 5/2003 | Winterbottom et al. |
| 2003/0100951 A1 | 5/2003 | Serhan et al. |
| 2003/0125739 A1 | 7/2003 | Bagga et al. |
| 2003/0130662 A1 | 7/2003 | Michelson |
| 2003/0135277 A1 | 7/2003 | Bryan et al. |
| 2003/0139812 A1 | 7/2003 | Garcia et al. |
| 2003/0187448 A1 | 10/2003 | Michelson |
| 2003/0191536 A1 | 10/2003 | Ferree |
| 2003/0195517 A1 | 10/2003 | Michelson |
| 2003/0195631 A1 | 10/2003 | Ferree |
| 2003/0199982 A1 | 10/2003 | Bryan |
| 2003/0199983 A1 | 10/2003 | Michelson |
| 2003/0204261 A1 | 10/2003 | Eisermann et al. |
| 2003/0208271 A1 | 11/2003 | Kuras |
| 2003/0229358 A1 | 12/2003 | Errico et al. |
| 2003/0233145 A1 | 12/2003 | Landry et al. |
| 2004/0002761 A1 | 1/2004 | Rogers et al. |
| 2004/0024407 A1 | 2/2004 | Ralph et al. |
| 2004/0024410 A1 | 2/2004 | Olson et al. |
| 2004/0030391 A1 | 2/2004 | Ferree |
| 2004/0034426 A1 | 2/2004 | Errico et al. |
| 2004/0054411 A1 | 3/2004 | Kelly et al. |
| 2004/0059318 A1 | 3/2004 | Zhang et al. |
| 2004/0073307 A1 | 4/2004 | Keller |
| 2004/0073311 A1 | 4/2004 | Ferree |
| 2004/0073312 A1 | 4/2004 | Eisermann et al. |
| 2004/0093087 A1 | 5/2004 | Ferree et al. |
| 2004/0097928 A1 | 5/2004 | Zdeblick et al. |
| 2004/0098131 A1 | 5/2004 | Bryan et al. |
| 2004/0117021 A1 | 6/2004 | Biedermann et al. |
| 2004/0143270 A1 | 7/2004 | Zucherman et al. |
| 2004/0143332 A1 | 7/2004 | Krueger et al. |
| 2004/0143334 A1 | 7/2004 | Ferree |
| 2004/0167626 A1 | 8/2004 | Geremakis et al. |
| 2004/0176843 A1 | 9/2004 | Zubok et al. |
| 2004/0186569 A1 | 9/2004 | Berry |
| 2004/0215342 A1 | 10/2004 | Suddaby |
| 2004/0225295 A1 | 11/2004 | Zubok et al. |
| 2004/0225365 A1 | 11/2004 | Eisermann et al. |
| 2004/0230307 A1* | 11/2004 | Eisermann .............. A61F 2/447 623/17.11 |
| 2004/0236426 A1 | 11/2004 | Ralph et al. |
| 2004/0243238 A1 | 12/2004 | Arnin et al. |
| 2004/0254644 A1 | 12/2004 | Taylor |
| 2005/0015094 A1 | 1/2005 | Keller |
| 2005/0015095 A1 | 1/2005 | Keller |
| 2005/0015152 A1 | 1/2005 | Sweeney |
| 2005/0021145 A1 | 1/2005 | De et al. |
| 2005/0021146 A1 | 1/2005 | De et al. |
| 2005/0027360 A1 | 2/2005 | Webb et al. |
| 2005/0038515 A1 | 2/2005 | Kunzler |
| 2005/0043800 A1 | 2/2005 | Paul et al. |
| 2005/0085917 A1 | 4/2005 | Marnay et al. |
| 2005/0107881 A1 | 5/2005 | Alleyne et al. |
| 2005/0113842 A1 | 5/2005 | Bertagnoli et al. |
| 2005/0113928 A1 | 5/2005 | Cragg et al. |
| 2005/0143824 A1 | 6/2005 | Richelsoph et al. |
| 2005/0149189 A1 | 7/2005 | Mokhtar et al. |
| 2005/0154463 A1 | 7/2005 | Trieu |
| 2005/0165408 A1 | 7/2005 | Puno et al. |
| 2005/0171604 A1 | 8/2005 | Michalow |
| 2005/0187634 A1 | 8/2005 | Berry |
| 2005/0192586 A1 | 9/2005 | Zucherman et al. |
| 2005/0192670 A1 | 9/2005 | Zubok et al. |
| 2005/0197706 A1 | 9/2005 | Hovorka et al. |
| 2005/0216081 A1 | 9/2005 | Taylor et al. |
| 2005/0216084 A1 | 9/2005 | Fleischmann et al. |
| 2005/0234553 A1 | 10/2005 | Gordon |
| 2005/0251260 A1 | 11/2005 | Gerber et al. |
| 2005/0251261 A1 | 11/2005 | Peterman |
| 2005/0261772 A1 | 11/2005 | Filippi et al. |
| 2005/0267580 A1 | 12/2005 | Suddaby |
| 2005/0267581 A1 | 12/2005 | Marnay et al. |
| 2006/0004377 A1 | 1/2006 | Keller |
| 2006/0004453 A1 | 1/2006 | Bartish et al. |
| 2006/0015183 A1 | 1/2006 | Gilbert et al. |
| 2006/0020342 A1 | 1/2006 | Ferree et al. |
| 2006/0025862 A1 | 2/2006 | Villiers et al. |
| 2006/0030862 A1 | 2/2006 | De et al. |
| 2006/0036325 A1 | 2/2006 | Paul et al. |
| 2006/0041313 A1 | 2/2006 | Allard et al. |
| 2006/0041314 A1 | 2/2006 | Millard |
| 2006/0052870 A1 | 3/2006 | Ferree |
| 2006/0064169 A1 | 3/2006 | Ferree |
| 2006/0069439 A1 | 3/2006 | Zucherman et al. |
| 2006/0116768 A1 | 6/2006 | Krueger et al. |
| 2006/0136061 A1 | 6/2006 | Navarro et al. |
| 2006/0142858 A1 | 6/2006 | Colleran et al. |
| 2006/0142862 A1 | 6/2006 | Diaz et al. |
| 2006/0155378 A1 | 7/2006 | Eckman |
| 2006/0167549 A1 | 7/2006 | Mathys, Jr. et al. |
| 2006/0178744 A1 | 8/2006 | De et al. |
| 2006/0178746 A1 | 8/2006 | Bartish et al. |
| 2006/0195097 A1 | 8/2006 | Evans et al. |
| 2006/0200239 A1 | 9/2006 | Rothman et al. |
| 2006/0200240 A1 | 9/2006 | Rothman et al. |
| 2006/0200242 A1 | 9/2006 | Rothman et al. |
| 2006/0200243 A1 | 9/2006 | Rothman et al. |
| 2006/0224241 A1 | 10/2006 | Butler et al. |
| 2006/0235426 A1 | 10/2006 | Lim et al. |
| 2006/0235525 A1 | 10/2006 | Gil et al. |
| 2006/0235527 A1 | 10/2006 | Buettner-Janz et al. |
| 2006/0241641 A1 | 10/2006 | Albans et al. |
| 2006/0241766 A1 | 10/2006 | Felton et al. |
| 2006/0259144 A1 | 11/2006 | Trieu |
| 2006/0259146 A1 | 11/2006 | Navarro et al. |
| 2006/0265068 A1 | 11/2006 | Schwab |
| 2006/0265077 A1 | 11/2006 | Zwirkoski |
| 2006/0276902 A1 | 12/2006 | Zipnick et al. |
| 2006/0287728 A1 | 12/2006 | Mokhtar et al. |
| 2006/0293752 A1 | 12/2006 | Moumene et al. |
| 2006/0293753 A1 | 12/2006 | Thramann |
| 2006/0293754 A1 | 12/2006 | Devilliers et al. |
| 2007/0010826 A1 | 1/2007 | Rhoda et al. |
| 2007/0021837 A1 | 1/2007 | Ashman |
| 2007/0032875 A1 | 2/2007 | Blacklock et al. |
| 2007/0067035 A1 | 3/2007 | Falahee |
| 2007/0067036 A1 | 3/2007 | Hudgins et al. |
| 2007/0073398 A1 | 3/2007 | Fabian et al. |
| 2007/0093898 A1 | 4/2007 | Schwab et al. |
| 2007/0100453 A1 | 5/2007 | Parsons et al. |
| 2007/0100454 A1 | 5/2007 | Burgess et al. |
| 2007/0100456 A1 | 5/2007 | Dooris et al. |
| 2007/0123903 A1 | 5/2007 | Raymond et al. |
| 2007/0123904 A1 | 5/2007 | Stad et al. |
| 2007/0135923 A1 | 6/2007 | Peterman et al. |
| 2007/0162133 A1 | 7/2007 | Doubler et al. |
| 2007/0168033 A1 | 7/2007 | Kim et al. |
| 2007/0168036 A1 | 7/2007 | Ainsworth et al. |
| 2007/0179615 A1 | 8/2007 | Heinz et al. |
| 2007/0213821 A1 | 9/2007 | Kwak et al. |
| 2007/0233077 A1 | 10/2007 | Khalili |
| 2007/0233247 A1 | 10/2007 | Schwab |
| 2007/0233248 A1 | 10/2007 | Schwab et al. |
| 2007/0233251 A1 | 10/2007 | Abdou |
| 2007/0270956 A1* | 11/2007 | Heinz ...................... A61F 2/44 623/17.11 |
| 2007/0270970 A1 | 11/2007 | Trieu |
| 2007/0282449 A1 | 12/2007 | De et al. |
| 2007/0299521 A1 | 12/2007 | Glenn et al. |
| 2008/0015698 A1 | 1/2008 | Marino et al. |
| 2008/0015701 A1 | 1/2008 | Garcia et al. |
| 2008/0021557 A1 | 1/2008 | Trieu |
| 2008/0051900 A1 | 2/2008 | De et al. |
| 2008/0051901 A1 | 2/2008 | De et al. |
| 2008/0125864 A1 | 5/2008 | De et al. |
| 2008/0125865 A1 | 5/2008 | Abdelgany et al. |
| 2008/0133011 A1 | 6/2008 | De et al. |
| 2008/0154301 A1 | 6/2008 | De et al. |

(56) References Cited

U.S. PATENT DOCUMENTS

| | | |
|---|---|---|
| 2008/0154305 A1* | 6/2008 | Foley .................. A61B 17/1604 606/247 |
| 2008/0154382 A1 | 6/2008 | De et al. |
| 2008/0161926 A1 | 7/2008 | Melkent et al. |
| 2008/0215155 A1 | 9/2008 | De et al. |
| 2008/0221696 A1 | 9/2008 | De et al. |
| 2008/0228274 A1 | 9/2008 | De et al. |
| 2008/0228277 A1 | 9/2008 | De et al. |
| 2008/0294259 A1 | 11/2008 | De et al. |
| 2009/0043391 A1 | 2/2009 | De et al. |
| 2009/0048674 A1 | 2/2009 | Zubok et al. |
| 2009/0048677 A1 | 2/2009 | Mcleod et al. |
| 2009/0076614 A1 | 3/2009 | Arramon |
| 2009/0105833 A1 | 4/2009 | Hovda et al. |
| 2009/0105834 A1* | 4/2009 | Hovda .................. A61F 2/4465 623/17.16 |
| 2009/0105835 A1 | 4/2009 | Hovda et al. |
| 2009/0118836 A1 | 5/2009 | Cordaro |
| 2009/0192617 A1 | 7/2009 | Arramon et al. |
| 2009/0205188 A1 | 8/2009 | De et al. |
| 2009/0210060 A1 | 8/2009 | De et al. |
| 2009/0222101 A1 | 9/2009 | De et al. |
| 2009/0276051 A1 | 11/2009 | Arramon et al. |
| 2009/0326656 A1 | 12/2009 | De et al. |
| 2010/0004746 A1 | 1/2010 | Arramon |
| 2010/0004748 A1 | 1/2010 | Cordaro |
| 2010/0016972 A1 | 1/2010 | Jansen et al. |
| 2010/0016973 A1 | 1/2010 | De et al. |
| 2010/0030335 A1 | 2/2010 | Arramon |
| 2010/0049040 A1 | 2/2010 | De et al. |
| 2010/0069976 A1 | 3/2010 | De et al. |
| 2010/0076558 A1 | 3/2010 | De et al. |
| 2010/0087868 A1 | 4/2010 | Barr et al. |
| 2010/0100141 A1 | 4/2010 | De et al. |
| 2010/0179419 A1 | 7/2010 | De et al. |
| 2010/0268344 A1 | 10/2010 | De et al. |

FOREIGN PATENT DOCUMENTS

| | | |
|---|---|---|
| EP | 0333990 A2 | 9/1989 |
| EP | 0333990 A3 | 5/1990 |
| EP | 0560140 A1 | 9/1993 |
| EP | 0560141 A1 | 9/1993 |
| EP | 0591712 A1 | 4/1994 |
| EP | 0820740 A1 | 1/1998 |
| EP | 1142544 A1 | 10/2001 |
| EP | 1153582 A2 | 11/2001 |
| EP | 1153582 A3 | 11/2001 |
| EP | 1250898 A1 | 10/2002 |
| EP | 1306064 A1 | 5/2003 |
| EP | 1344493 A1 | 9/2003 |
| EP | 1344506 A1 | 9/2003 |
| EP | 1344507 A1 | 9/2003 |
| EP | 1344508 A1 | 9/2003 |
| EP | 1417940 A1 | 5/2004 |
| EP | 1570813 A1 | 9/2005 |
| FR | 2803741 A1 | 7/2001 |
| JP | S61122859 A | 6/1986 |
| JP | S63164948 A | 7/1988 |
| WO | WO-9920209 A1 | 4/1999 |
| WO | WO-9930651 A1 | 6/1999 |
| WO | WO-0004851 A1 | 2/2000 |
| WO | WO-0035384 A1 | 6/2000 |
| WO | WO-0042954 A2 | 7/2000 |
| WO | WO-0042954 A3 | 11/2000 |
| WO | WO-0101893 A1 | 1/2001 |
| WO | WO-0115637 A1 | 3/2001 |
| WO | WO-0168003 A1 | 9/2001 |
| WO | WO-0211650 A2 | 2/2002 |
| WO | WO-0211650 A3 | 9/2003 |
| WO | WO-2004000170 A1 | 12/2003 |
| WO | WO-2004000171 A1 | 12/2003 |
| WO | WO-2004026187 A1 | 4/2004 |
| WO | WO-2004054477 A1 | 7/2004 |
| WO | WO-2005004756 A2 | 1/2005 |
| WO | WO-2005004756 A3 | 5/2005 |
| WO | WO-2005053580 A1 | 6/2005 |
| WO | WO-2005072662 A1 | 8/2005 |
| WO | WO-2005112834 A2 | 12/2005 |
| WO | WO-2005112834 A3 | 5/2006 |
| WO | WO-2006119092 A2 | 11/2006 |
| WO | WO-2006119092 A3 | 12/2006 |
| WO | WO-2007121320 A2 | 10/2007 |
| WO | WO-2007121320 A3 | 6/2008 |
| ZA | 20039312 | 11/2003 |

OTHER PUBLICATIONS

Chadwick, et al., Radiolucent Structural Materials for Medical Applications, Jun. 1, 2001, MODI, 1 page. Website Accessed Mar. 27, 2017 http://www.mddionline.com/article/radiolucent-structural-materials-medical-applications.

Co-pending U.S. Appl. No. 15/191,385, filed Jun. 23, 2016.

Hellier, et al., Wear Studies for Development of an Intervertebral Disc Prosthesis. Spine, vol. 17 No. 6 Supplement pp. 86-96 (1992).

International search report and written opinion dated Dec. 16, 2008 for PCT/US2008/080800.

International search report and written opinion dated Dec. 19, 2008 for PCT/US2008/080798.

International search report and written opinion dated Dec. 29, 2008 for PCT/US2008/080804.

Lee, et al. Impact Response of the Intervertebral Disc in a Finite-Element Model. Spine. 2000; 25(19):2431-2439.

Lehuec, et al. Shock Absorption in Lumber Disc Prosthesis. Journal of Spinal Disorders & Techniques. 2003; 16(4):346-351.

Office action dated Apr. 18, 2012 for U.S. Appl. No. 12/255,733.
Office action dated May 13, 2011 for U.S. Appl. No. 12/255,737.
Office action dated Jun. 7, 2011 for U.S. Appl. No. 12/255,731.
Office action dated Feb. 8, 2012 for U.S. Appl. No. 12/255,731.
Office action dated Aug. 14, 2013 for U.S. Appl. No. 12/255,731.
Office action dated Nov. 23, 2012 for U.S. Appl. No. 12/255,731.
Office action dated Apr. 6, 2017 for U.S. Appl. No. 15/191,385.
Office action dated Jun. 19, 2012 for U.S. Appl. No. 12/255,737.
Office action dated Aug. 26, 2011 for U.S. Appl. No. 12/255,733.
Office action dated Nov. 28, 2012 for U.S. Appl. No. 12/255,733.
Office action dated Dec. 15, 2011 for U.S. Appl. No. 12/255,737.
Office action dated Dec. 18, 2012 for U.S. Appl. No. 12/255,737.
"Office Action dated Nov. 13, 2017 for U.S. Appl. No. 15/191,385".

* cited by examiner

METHOD AND SPACER DEVICE FOR SPANNING A SPACE FORMED UPON REMOVAL OF AN INTERVERTEBRAL DISC

CROSS-REFERENCES TO RELATED APPLICATIONS

The present application is a continuation of U.S. patent application Ser. No. 12/255,731, filed Oct. 22, 2008, which claims priority from U.S. Provisional Patent Application No. 60/981,665, filed Oct. 22, 2007, the full disclosures of which are incorporated herein by reference.

BACKGROUND OF THE INVENTION

The present invention relates to medical devices and methods. More specifically, the invention relates to intervertebral spacers and methods of spanning a space formed upon removal of an intervertebral disc.

Back pain takes an enormous toll on the health and productivity of people around the world. According to the American Academy of Orthopedic Surgeons, approximately 80 percent of Americans will experience back pain at some time in their life. In the year 2000, approximately 26 million visits were made to physicians' offices due to back problems in the United States. On any one day, it is estimated that 5% of the working population in America is disabled by back pain.

One common cause of back pain is injury, degeneration and/or dysfunction of one or more intervertebral discs. Intervertebral discs are the soft tissue structures located between each of the thirty-three vertebral bones that make up the vertebral (spinal) column. Essentially, the discs allow the vertebrae to move relative to one another. The vertebral column and discs are vital anatomical structures, in that they form a central axis that supports the head and torso, allow for movement of the back, and protect the spinal cord, which passes through the vertebrae in proximity to the discs.

Discs often become damaged due to wear and tear or acute injury. For example, discs may bulge (herniate), tear, rupture, degenerate or the like. A bulging disc may press against the spinal cord or a nerve exiting the spinal cord, causing "radicular" pain (pain in one or more extremities caused by impingement of a nerve root). Degeneration or other damage to a disc may cause a loss of "disc height," meaning that the natural space between two vertebrae decreases. Decreased disc height may cause a disc to bulge, facet loads to increase, two vertebrae to rub together in an unnatural way and/or increased pressure on certain parts of the vertebrae and/or nerve roots, thus causing pain. In general, chronic and acute damage to intervertebral discs is a common source of back related pain and loss of mobility.

When one or more damaged intervertebral discs cause a patient pain and discomfort, surgery is often required. Traditionally, surgical procedures for treating intervertebral discs have involved discectomy (partial or total removal of a disc), with or without interbody fusion of the two vertebrae adjacent to the disc. When the disc is partially or completely removed, it is necessary to replace the excised material to prevent direct contact between hard bony surfaces of adjacent vertebrae. Oftentimes, pins, rods, screws, cages and/or the like are inserted between the vertebrae to act as support structures to hold the vertebrae and graft material in place while they permanently fuse together.

One typical fusion procedure is achieved by inserting a "cage" that maintains the space usually occupied by the disc to prevent the vertebrae from collapsing and impinging the nerve roots. The cage is used in combination with bone graft material (either autograft or allograft) such that the two vertebrae and the graft material will grow together over time forming bridging bone between the two vertebrae. The fusion process typically takes 6-12 months after surgery. During in this time external bracing (orthotics) may be required. External factors such as smoking, osteoporosis, certain medications, and heavy activity can prolong or even prevent the fusion process. If fusion does not occur, patients may require reoperation.

One known fusion cage is described in U.S. Pat. No. 4,904,261 and includes a horseshoe shaped body. This type cage is currently available in PEEK (polyetheretherketone). PEEK is used because it does not distort MRI and CT images of the vertebrae. However, PEEK is a material that does not allow bone to attach. Thus, fusion with a PEEK cage requires bridging bone to grow through the holes in the cage to provide stabilization.

It would be desirable to achieve immobilization of the vertebrae and maintain spacing between the adjacent vertebrae without the associated patient discomfort and long recovery time of traditional interbody fusion which may require immobilization for several months.

Another problem associated with the typical fusion procedure is the subsidence of the cage into the vertebral body. The typical fusion cage is formed with a large percentage of open space to allow the bone to grow through and form the bridging bone which immobilizes the discs. However, the large amount of open space means that the load on each segment of the cage is significantly higher than if the cage surface area was larger. This results in the cage subsiding or sinking into the bone over time causing the disc space to collapse. In addition, the hard cortical bone on the outer surface of the vertebral body that transfers load to the interbody cage or spacer is often scraped, punctured or otherwise damaged to provide blood to the interbody bone graft to facilitate bone growth. This damage to the bone used to promote bone growth can also lead to subsidence.

The U.S. Food and Drug Administration approved the use of a genetically engineered protein, or rhBMP-2, for certain types of spine fusion surgery. RhBMP-2 is a genetically engineered version of a naturally occurring protein that helps to stimulate bone growth, marketed by Medtronic Sofamor Danek, Inc. as InFUSE™ Bone Graft. When InFUSE™ is used with the bone graft material it eliminates the need for painful bone graft harvesting and improves patients' recovery time. However, InFUSE™ adds significantly to the cost of a typical fusion surgery. Additionally, even with the bone graft and InFUSE™ bone may fail to grow completely between the two vertebrae or the cage may subside into the vertebrae such that the fusion fails to achieve its purpose of maintaining disc height and preventing motion.

In an attempt to treat disc related pain without fusion and to maintain motion, an alternative approach has been developed, in which a movable, implantable, artificial intervertebral disc (or "disc prosthesis") is inserted between two vertebrae. A number of different artificial intervertebral discs are currently being developed. For example, U.S. Patent Application Publication Nos. 2005/0021146, 2005/0021145, and 2006/0025862, which are hereby incorporated by reference in their entirety, describe artificial intervertebral discs. Other examples of intervertebral disc prostheses are the LINK SB CHARITLE™ disc prosthesis (provided by DePuy Spine, Inc.) the MOBIDISK™ disc prosthesis (provided by LDR Medical), the BRYAN™ cervical disc prosthesis (provided by Medtronic Sofamor Danek, Inc.), the PRODISC™ disc prosthesis or PRODISC-C™ disc prosthesis (from Synthes Stratec, Inc.), the PCM™ disc prosthesis (provided by Cervitech, Inc.), and the MAVERICK™ disc prosthesis (provided by Medtronic Sofomor Danek). Although existing disc prostheses provide advantages over traditional treatment methods, many patients are not candidates for an artificial disc due to facet degeneration, instability, poor bone strength, previous surgery, multi-level disease, and pain sources that are non-discogenic.

Therefore, a need exists for an improved spacer and method for spanning a space and maintaining disc spacing between two vertebrae after removal of an intervertebral disc. Ideally, such improved method and spacer would avoid the need for growth of bridging bone across the intervertebral space.

BRIEF SUMMARY OF THE INVENTION

Embodiments of the present invention provide a rigid intervertebral spacer and methods of spanning a space formed upon removal of an intervertebral disc.

In accordance with one aspect of the present invention, a method of spanning a space formed by upon removal of an intervertebral disc includes the steps of performing a discectomy to remove disc material between two adjacent vertebral bodies; placing an intervertebral spacer between the two adjacent vertebral bodies; and maintaining the disc space between the two adjacent vertebral bodies with the intervertebral spacer without the use of bone graft or bridging bone. The spacer includes two end plates, each end plate having a metallic vertebral body contacting surface and an inner surface, and a connector interconnecting the inner surfaces of the two end plates in a rigid manner which limits motion between the plates to less than a total of 5 degrees. The vertebral body contacting surfaces of the end plates have no holes therein or have holes which cover less than 40 percent of the vertebral body contacting surface.

In accordance with another aspect of the present invention, an intervertebral spacer for spanning a space formed by upon removal of an intervertebral disc includes two end plates sized and shaped to fit within an intervertebral space and a connector interconnecting the inner surfaces of the two end plates in a rigid manner which limits motion between the plates to less than a total of 5 degrees. Each end plate has a metallic vertebral contacting surface and an inner surface and the vertebral body contacting surfaces of the end plates have no holes therein or have holes which cover less than 40 percent of the vertebral body contacting surfaces.

In accordance with a further aspect of the invention, a method of performing an anterior/posterior fusion comprises performing a discectomy to remove disc material between two adjacent vertebral bodies; placing an intervertebral spacer between the two adjacent discs; maintaining the disc space between the two adjacent discs with the intervertebral spacer; and posteriorly placing a stabilization system to fix the angle between the vertebral bodies. The spacer includes two end plates each having a metallic vertebral contacting surface and an inner surface, and a rigid connector interconnecting the inner surfaces of the two end plates. The vertebral body contacting surfaces of the end plates have no holes therein or have holes which cover less than 40 percent of the vertebral body contacting surfaces.

In accordance with another aspect of the invention, a fusion system includes an intervertebral spacer and a posteriorly placed stabilization system including at least two screws configured to be placed into the vertebral bodies and at least one connector there between, The intervertebral spacer includes two end plates sized and shaped to fit within an intervertebral space, each end plate having a vertebral contacting surface an inner surface and a rigid connector interconnecting the inner surfaces of the two end plates. The vertebral body contacting surfaces of the end plates have no holes therein or have holes which cover less than 40 percent of the vertebral body contacting surfaces.

In accordance with an additional aspect of the invention, a fusion spacer includes a rigid spacer body sized and shaped to fit within an intervertebral space between two vertebral bodies, the body having two opposed metallic vertebral contacting surfaces; at least one fin extending from each of the vertebral contacting surfaces, the fins configured to be positioned within slots cut into the two vertebral bodies; and a plurality of serrations on the vertebral contacting surfaces. Holes, if present, cover less than 40 percent of the entire vertebral body contacting surfaces.

BRIEF DESCRIPTION OF THE DRAWINGS

FIG. 5B is an anterior view of an intervertebral spacer with

DETAILED DESCRIPTION OF THE INVENTION

Various embodiments of the present invention generally provide for an intervertebral spacer having upper and lower plates connected by a central connector which is substantially rigid. The intervertebral spacer according to the present invention can maintain disc height and prevent subsidence with a large vertebral body contacting surface area while substantially reducing recovery time by eliminating the need for bridging bone. The fusion spacer described herein is designed particularly for patients who are not candidates for total disc replacement.

Figure 1:
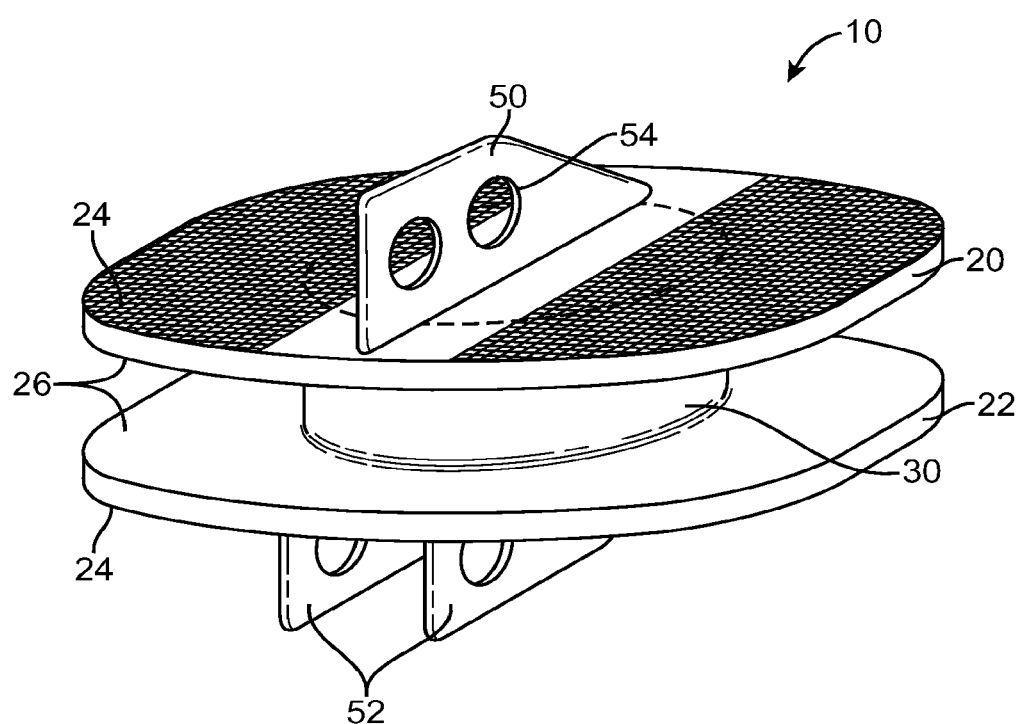
FIG. 1 is a perspective view of an intervertebral spacer according to one embodiment of the present invention.

One example of an intervertebral spacer 10 for maintaining disc height between two adjacent vertebral discs is shown in FIG. 1. The spacer includes two end plates 20, 22, each end plate having a vertebral contacting surface 24 and an inner surface 26, and a connector 30 interconnecting the inner surfaces of the two end plates in a substantially rigid manner. The intervertebral spacer 10 when implanted between two vertebral discs maintains a desirable disc space between the two adjacent discs similar to that provided by a natural disc and eliminates the long recovery time required to grow bridging bone which is required in the traditional fusion surgery.

Although the connector 30 has been shown as circular in cross section, other shapes may be used including oval, elliptical, or rectangular. Although the connector has been shown as a solid member connecting the plates 20, 22 in the center of the plates one or more connectors may be provided in other configurations and at other locations. By way of example, a connector may be the same or substantially the same diameter and shape as the plate, as in FIGS. 6 and 7. Alternatively, multiple connectors can be arranged in a pattern, such as a rectangular pattern, or a hollow cylindrical connector can be used.

Figure 2:
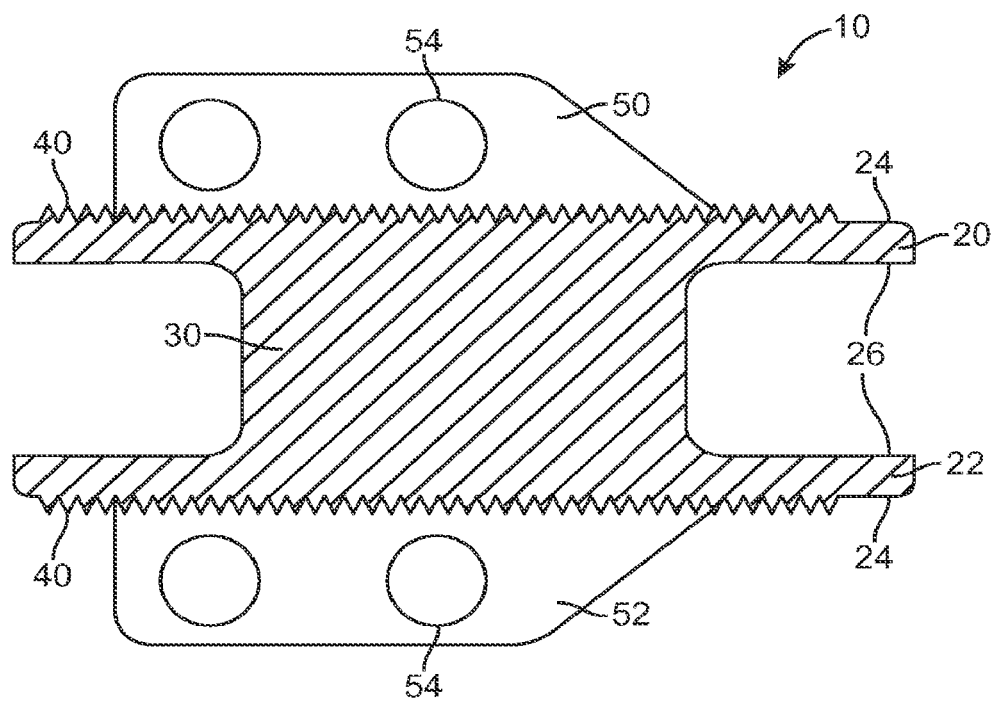
FIG. 2 is a cross sectional side view of the intervertebral spacer of FIG. 1.
Figure 3:
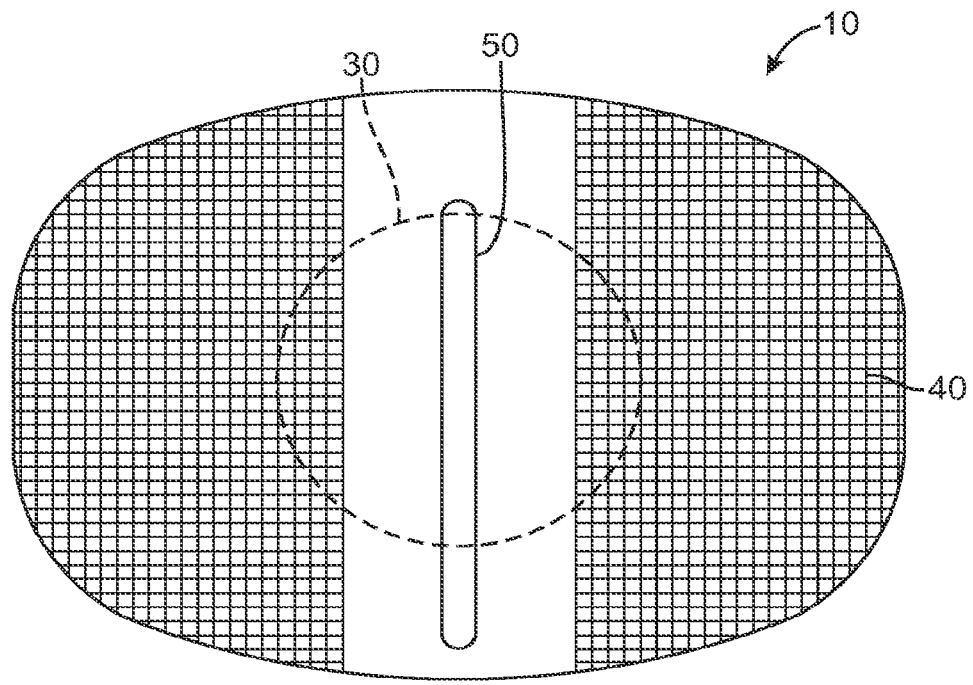
FIG. 3 is a top view of the intervertebral spacer of FIG. 1.
Figure 4:
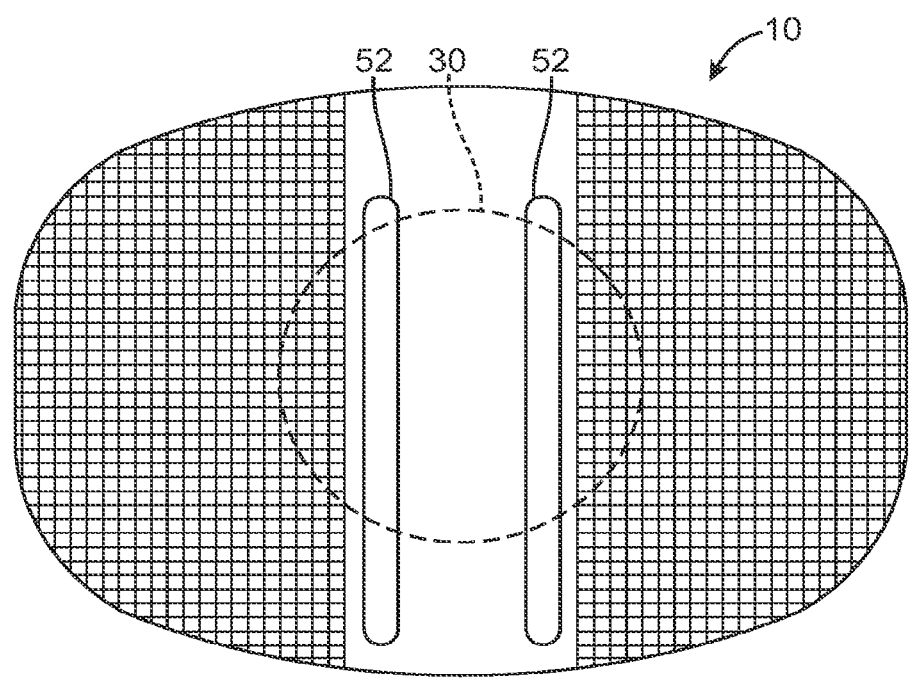
FIG. 4 is a bottom view of the intervertebral spacer of FIG. 1.

In some embodiments, the outer surface 24 is planar. Oftentimes, the outer surface 24 will include one or more surface features and/or materials to enhance attachment of the spacer 10 to vertebral bone. For example, as shown in FIG. 2, the outer surface 24 may be machined to have serrations 40 or other surface features for promoting adhesion of the plates 20, 22 to a vertebra. In the embodiments shown, the serrations 40 are pyramid shaped serrations extending in mutually orthogonal directions and arranged on opposite sides of a fin 50. The serrations 40 may also be disposed in a region between fins 52 when the outer surface 24 has two fins. Other geometries such as teeth, grooves, ridges, pins, barbs or the like would also be useful in increasing fixation of the spacer 10 to the adjacent vertebral bodies. When the bone integration structures are ridges, teeth, barbs or similar structures, they may be angled to ease insertion and prevent migration. These bone integration structures can be used to precisely cut the bone during implantation to cause bleeding bone and encourage bone integration. Additionally, the outer surface 24 may be provided with a rough microfinish formed by blasting with aluminum oxide microparticles or the like to improve bone integration. In some embodiments, the outer surface may also be titanium plasma sprayed or HA coated to further enhance attachment of the outer surface 24 to vertebral bone.

The outer surface 24 may also carry one or more upstanding fins 50, 52 extending in an anterior-posterior direction. The fins 50, 52 are configured to be placed in slots cut into the vertebral bodies. Preferably, the fins 50, 52 each have a height greater than a width and have a length greater than the height. In one embodiment, the fins 50, 52 are pierced by transverse holes 54 for bone ingrowth. The transverse holes 54 may be formed in any shape and may extend partially or all the way through the fins 50, 52. In alternative embodiments, the fins 50, 52 may be rotated away from the anterior-posterior axis, such as in a lateral-lateral orientation, a posterolateral-anterolateral orientation, or the like to accommodate alternate implantation approaches.

The fins 50, 52 provide improved attachment to the bone and prevent rotation of the plates 20, 22 in the bone. In some embodiments, the fins 50, 52 may extend from the surface 24 at an angle other than 90°. For example, on one or more of the plates 20, 22 where multiple fins 52a are attached to the surface 24 the fins 52a may be canted away from one another with the bases slightly closer together than their edges at an angle such as about 80-88 degrees, as shown in FIG. 5A. The fins 50, 52 may have any other suitable configuration including various numbers, angles and curvatures, in various embodiments. In some embodiments, the fins 50, 52 may be omitted altogether. The embodiment of FIG. 1 illustrates a combination of a first plate 20 with a single fin 50 and a second plate 22 with a double fin 52. This arrangement is useful for double level disc replacements and utilizes offset slots in the vertebral body to prevent the rare occurrence of vertebral body splitting by avoiding cuts to the vertebral body in the same plane for multi-level implants. FIG. 5B illustrates a combination of a first plate 20 with double fins 52 and a second plate 22 with double fins 52.

The spacer 10 has been shown with the fins 50, 52 as the primary fixation feature, however, the fins may also be augmented or replaced with one or more screws extending through the plates and into the bone. For example in the spacer 10 of FIG. 1 the upper fin 50 may be replaced with a screw while the two lower fins 52 remain. The plates 20, 22 can be provided with one or a series of holes to allow screws to be inserted at different locations at the option of the surgeon. However, the holes should not be of such size or number that the coverage of the plate 20, 22 is decreased to such an extent that subsidence occurs. When one or more screws are provided, they may incorporate a locking feature to prevent the screws from backing out. The screws may also be provided with a bone integration coating.

The upper and lower plates 20, 22 and connector 30 may be constructed from any suitable metal, alloy or combination of metals or alloys, such as but not limited to cobalt chrome alloys, titanium (such as grade 5 titanium), titanium based alloys, tantalum, nickel titanium alloys, stainless steel, and/or the like. They may also be formed of ceramics, biologically compatible polymers including PEEK, UHMWPE (ultra high molecular weight polyethlyne) or fiber reinforced polymers. However, the vertebral contacting surfaces 24 are formed of a metal or other material with good bone integration properties. The metallic vertebral body contacting surfaces 24 may be coated or otherwise covered with the metal for fixation. The plates 20, 22 and the connector 20 may be formed of a one piece construction or may be formed of more than one piece, such as different materials coupled together. When the spacer 10 is formed of multiple materials these materials are fixed together to form a unitary one piece spacer structure without separately moving parts.

Different materials may be used for different parts of the spacer 10 to optimize imaging characteristics. For example, the plates may be formed of titanium while the connector is formed of cobalt chromium alloy for improved imaging of the plates. Cobalt chrome molybdenum alloys when used for the plates 20, 22 may be treated with aluminum oxide blasting followed by a titanium plasma spray to improve bone integration. Other materials and coatings can also be used such as titanium coated with titanium nitride, aluminum oxide blasting, HA (hydroxylapatite) coating, micro HA coating, and/or bone integration promoting coatings. Any other suitable metals or combinations of metals may be used as well as ceramic or polymer materials, and combinations thereof. Any suitable technique may be used to couple materials together, such as snap fitting, slip fitting, lamination, interference fitting, use of adhesives, welding and/or the like.

Figure 5:
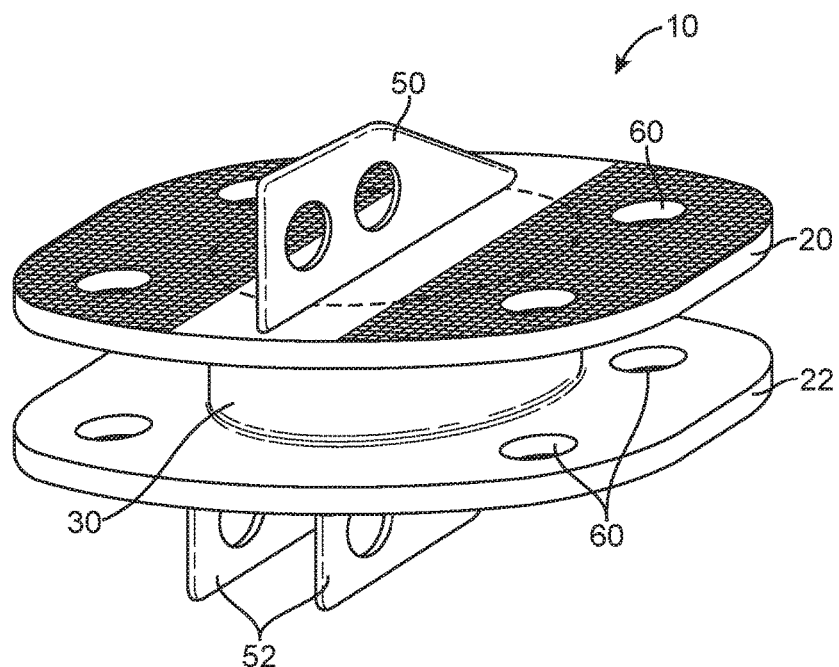
FIG. 5 is a perspective view of an intervertebral spacer according to another embodiment of the present invention.
Figure 5A:
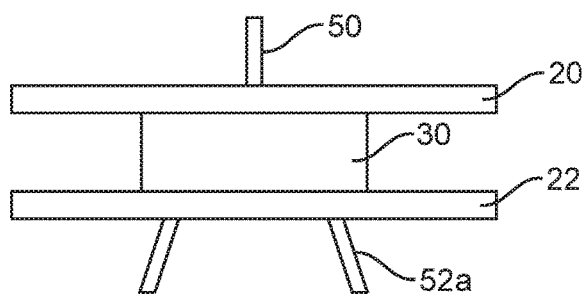
FIG. 5A is an anterior view of an intervertebral spacer with angled fins.
Figure 5B:
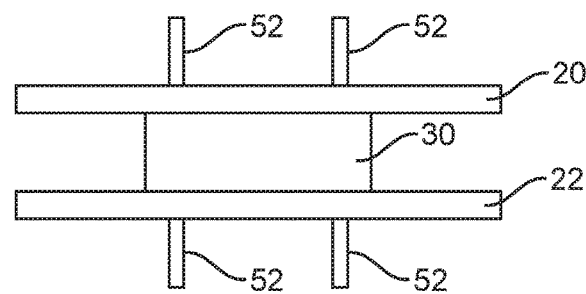

As shown in FIG. 5, some limited holes 60 may also be provided in the plates 20, 22 to allow bone in growth. Holes provided in a typical fusion spacer provide a spacer with little structural support and maximum area for bone growth. Thus, the load transferred across the disc space per unit area of spacer is quite high resulting in possible subsidence of the typical spacer. In the spacer 10 of the present invention, the load transfer is spread across a larger area. If the outer surfaces 24 have holes 60 therein, the holes will cover less than 40 percent of the outer surface 24 which contacts the bone to prevent subsidence of the plates into the vertebral bodies. Preferably the holes will cover less than 25 percent, and more preferably less than 10 percent of the outer bone contacting surfaces. At the option of the surgeon, when the small holes 60 are present in the plates 20, 22, bone graft can be placed in the space between the inner surfaces 26 of the plates to encourage bone to grow through the plates. The holes 60, when present can take on a variety of shapes including circular, as shown, rectangular, polygonal or other irregular shapes. The holes 60 may extend through the various parts of the spacer including through the connector or through the fins. The holes 60 may change shape or size as they pass through portions of the spacer, for example, holes through the plates and the connector may taper to a smaller interior diameter.

The typical fusion spacer requires bleeding bone to stimulate the growth of bridging bone. In this typical method, the cortical endplates are damaged purposefully to obtain bleeding by rasping or cutting the bone. This damage weakens the bone and can cause subsidence of the spacer. The spacer 10 described herein does not rely on bridging bone and does not require damaging the bone to cause bleeding. The spacer 10 can be implanted after simply cleaning the disc space and cutting slots into the vertebral endplates configured to receive the fins 50, 52. The rest of the endplates remain undamaged, providing better support and disc height maintenance.

Figure 6:
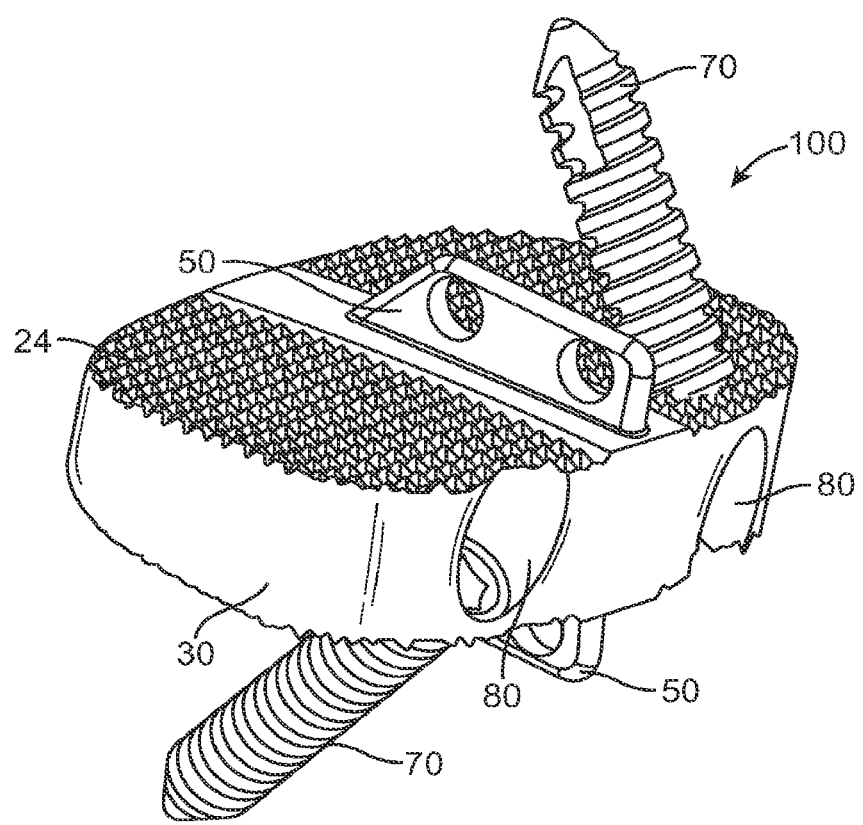
FIG. 6 is a perspective view of an intervertebral spacer according to an embodiment with added screw fixation.

FIG. 6 shows another embodiment of a spacer 100 having a single fin 50 on the top and bottom and two fixation screws 70 extending at an angle of about 30 to about 60 degrees with respect to the vertebral body contacting surfaces 24 of the spacer. The spacer 100 also includes a connector 30 between the vertebral body contacting surfaces 24 which is formed in one piece with the upper and lower plates. The fixation screws 70 can include a locking mechanism, such as a locking thread or a separate locking member which is inserted into the screw holes 80 after the screws are inserted to prevent backing out of the screws.

Figure 7:
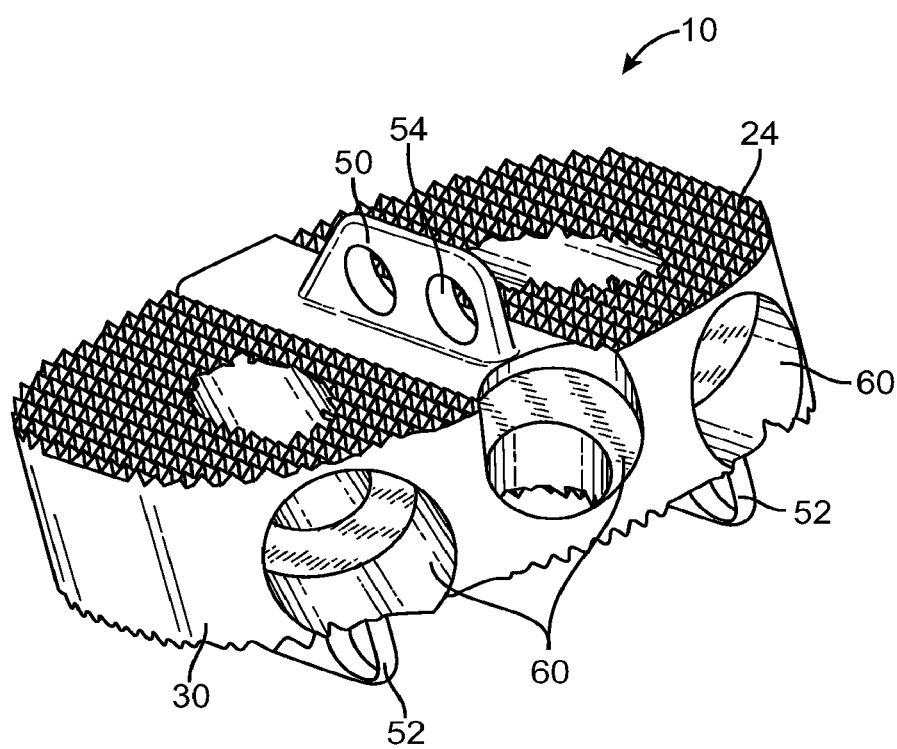
FIG. 7 is a perspective view of a further intervertebral spacer with added screw fixation.

FIG. 7 illustrates an alternative embodiment of a spacer 110 having a single superior fin 50, two inferior fins 52, and three alternating holes 80 for receiving bone screws (not shown). The spacer 110 has multiple fixation structures to provide the patient near immediate mobility after the fusion procedure. As an alternative to the alternating angled holes 80, the spacer 110 can be formed with an anterior flange extending from the top and the bottom at the anterior side of the plate. This optional flange can include one or more holes for receiving bone screws placed laterally. The laterally placed bone screws can prevent interference in the event of multilevel fusions and are particularly useful for a cervical fusion where space is more limited.

The intervertebral spacer 10 shown herein is configured for placement in a lumbar intervertebral space from an anterior approach. It should be understood that all approaches can be used including PLIF (posterior lumbar interbody fusion), TLIF (transverse lumbar interbody fusion), XLIF (Lateral extracavitary interbody fusion), ALIF (anterior lumbar interbody fusion), trans-sacral, and other approaches. The shape of the intervertebral spacer would be modified depending on the approach. For example, for a posterior approach, the spacer may include two separate smaller spacers which are either positioned separately side-by-side in the intervertebral space or two spacers which are joined together once inside the intervertebral space. For a lateral approach, the intervertebral spacer may be formed in a more elongated, kidney bean or banana shape with a transversely oriented fin.

The spacers 10, 100 can be provided in different sizes, with different plate sizes, angles between plates, lordosis angles, and heights for different patients or applications. The spacers 10, 100 are primarily designed for use in the lumbar spine, however the spacers may also be used for fusions of the cervical spine. In one variation, the height of the spacer can be adjustable, such as by rotating an adjustment screw in the connector 30 before or after implantation. The spacers preferably are sized to provide substantial coverage of the vertebral surfaces. For example in an anterior procedure, the plates are sized to cover at least 50 percent of the vertebral surface, and preferably cover at least 70 percent of the vertebral surface. In posterior or lateral procedures the coverage of the vertebral surface may be somewhat smaller due to the small size of the access area, i.e. the posterior or lateral spacers may cover about 40 percent or more of the vertebral surface with a one or two part spacer, and preferably at least 50 percent of the vertebral surface.

The size of the intervertebral spacers 10, 100, 110 can also be described in terms of the amount of the volume of the intervertebral space occupied by the spacer. According to a preferred embodiment, the total volume of the intervertebral spacer selected for a particular intervertebral space fills at least 50 percent of the volume of the space available between the adjacent vertebrae. More preferably, the volume of the spacer is at least 70 percent of the volume of the intervertebral space. The volume of the intervertebral space is defined as the volume of the space between the vertebrae when the vertebrae are distracted to a normal physiologic position for the particular patient without over or under distracting. The size of the intervertebral spacers 10, 100, 110 can also be determined by the amount of the support provided to the ring of cortical bone surrounding each vertebrae. The cortical bone surrounds a more spongy cancellous. Preferably, the intervertebral spacer is selected to support at least 75 percent of the diameter of the ring of cortical bone.

One common fusion procedure, referred to as an anterior/posterior fusion, uses of one or more fusion cages to maintain the disc space while bridging bone grows and also uses a system of posterior screws and rods for further stabilization. Fusing both the front and back provides a high degree of stability for the spine and a large surface area for the bone fusion to occur. Also, approaching both sides of the spine often allows for a more aggressive reduction of motion for patients who have deformity in the lower back (e.g. isthmic spondylolisthesis).

According to a method of the present invention, the anterior approach is performed first by removing the disc material and cutting the anterior longitudinal ligament (which lays on the front of the disc space). The spacer is positioned anteriorly and then the patient is turned over for the implantation of a posterior stabilization system. The intervertebral spacers of the present invention may be used in combination with a posterior stabilization system, dynamic rod stabilization system, or interspinous spacer to achieve the anterior/posterior fusion.

In another example, a posterior intervertebral spacer formed in two parts can be used with a posterior stabilization system including screws and rods. This system provides the advantage of maintenance of disc height and stabilization with an entirely posterior approach.

While the exemplary embodiments have been described in some detail, by way of example and for clarity of understanding, those of skill in the art will recognize that a variety of modifications, adaptations, and changes may be employed. Hence, the scope of the present invention should be limited solely by the appended claims.

What is claimed is:

1. A method of spanning a space formed upon removal of an intervertebral disc, the method comprising:
   performing a discectomy to remove disc material between two adjacent vertebral bodies;
   cutting at least one slot in at least one of the adjacent vertebral bodies;

placing an intervertebral spacer between the two adjacent vertebral bodies, the spacer comprising:
  two end plates, each end plate having a metallic vertebral body contacting surface, an inner surface and a fin extending from the vertebral body contacting surfaces;
  a connector interconnecting the inner surfaces of the two end plates in a rigid manner which limits motion between the end plates, the connector being a solid cylindrical member;
  wherein each of the vertebral body contacting surfaces of the end plates have no holes therein or have holes which cover only a portion of the vertebral body contacting surfaces;
  wherein the intervertebral spacer including the two end plates and connector is formed of a single piece;
placing the fin of one of the end plates into the at least one slot, thereby inhibiting rotation of the spacer relative to the at least one adjacent vertebral body having the at least one slot; and
maintaining the disc space between the two adjacent vertebral bodies with the intervertebral spacer without the use of bone graft or bridging bone, wherein no part of the intervertebral spacer extends outside the intervertebral disc space.

2. The method of claim 1, wherein the connector is a rigid connector.

3. The method of claim 1, wherein the two end plates and connector are formed of a single piece of metal.

4. The method of claim 1, wherein the intervertebral spacer is selected, such that when the spacer is positioned between the adjacent vertebral bodies the spacer fills at least 50 percent of a vertebral space formed between the adjacent vertebral bodies.

5. The method of claim 1, wherein each of the vertebral body contacting surfaces of the end plates has holes which cover less than 25 percent of the vertebral body contacting surfaces.

6. The method of claim 1, further comprising at least one fixation means provided on each of the vertebral body contacting surfaces the intervertebral spacer.

7. The method of claim 6, wherein the fixation means is at least one of a screw, teeth, serrations, or grooves.

8. The method of claim 1, wherein at least one of the metallic vertebral contacting surfaces is formed of titanium or a titanium alloy.

9. The method of claim 1, wherein the two adjacent vertebral bodies are stabilized without the use of external plates or screws.

10. The method of claim 1, wherein the two end plates and connector are formed of a single piece of PEEK with metallic vertebral body contacting surfaces.

11. The method of claim 1, wherein the fin on each of the two end plates comprises two fins.

12. The method of claim 1, wherein the fin includes at least two canted fins, the at least two canted fins are not perpendicular to the metallic vertebral body contacting surface of each end plate.

13. The method of claim 1, wherein the fin includes parallel opposite side surfaces.

14. An intervertebral spacer for spanning a space formed upon removal of an intervertebral disc, the spacer comprising:
  two end plates sized and shaped to fit within an intervertebral space between two vertebrae, each end plate having a metallic vertebral contacting surface and an inner surface;
  a connector interconnecting the inner surfaces of the two end plates in a rigid manner which limits motion between the end plates, the connector being a solid cylindrical member;
  at least one fin projecting from one of the vertebral contacting surfaces, wherein the at least one fin is configured to be inserted into a slot cut in at least one of the two vertebrae to inhibit rotation of the spacer with respect to the vertebrae, wherein at least one of the two end plates comprises two fins canted away from one another with bases of the two fins closer together than edges of the two fins; and
  wherein the two end plates and connector are formed of a single piece of PEEK with metallic screens or metallic coatings formed directly on the PEEK to provide the vertebral body contacting surfaces.

15. The spacer of claim 14, wherein each of the vertebral body contacting surfaces of the end plates include holes, and wherein the holes cover less than 40 percent of the vertebral body contacting surfaces.

16. The spacer of claim 14, wherein the intervertebral spacer is configured such that when placed within the intervertebral space no part of the intervertebral spacer extends outside the intervertebral disc space.

17. The spacer of claim 14, wherein the at least one fin on each of the two end plates comprises two fins.

18. The spacer of claim 14, wherein the at least one fin includes canted fins, the canted fins are not perpendicular to the metallic vertebral body contacting surface of each end plate.

19. The spacer of claim 14, wherein each of the at least one fin includes parallel opposite side surfaces.

20. An intervertebral spacer for spanning a space formed upon removal of an intervertebral disc, the spacer comprising:
  two end plates sized and shaped to fit within an intervertebral space between two adjacent vertebral bodies, each end plate having a vertebral contacting surface and an inner surface;
  a connector interconnecting the inner surfaces of the two end plates in a rigid manner which limits motion between the end plates, the connector being a solid cylindrical member;
  at least two fins projecting from each of the vertebral contacting surfaces, wherein the at least two fins are each configured to be inserted into a slot cut in the adjacent vertebral bodies to inhibit rotation of the spacer with respect to the adjacent vertebral bodies, and wherein the at least two fins on each end plate are canted away from one another, wherein the at least two fins are closer together at the at least two fins' respective bases than at the at least two fins' respective edges.

21. The spacer of claim 20, wherein each of the at least two fins include parallel opposite side surfaces.

* * * * *